(12) United States Patent
Fowler

(10) Patent No.: US 6,488,916 B1
(45) Date of Patent: Dec. 3, 2002

(54) SKIN CARE COMPOSITIONS

(75) Inventor: Kevin Fowler, Millington, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/103,924

(22) Filed: Mar. 22, 2002

Related U.S. Application Data

(63) Continuation of application No. 09/813,614, filed on Mar. 21, 2001, now Pat. No. 6,391,290.

(51) Int. Cl.[7] .............................. A61K 7/42; A61K 7/00; A01N 25/00; B01F 3/08

(52) U.S. Cl. .................. 424/59; 424/400; 424/401; 424/405; 424/DIG. 5; 514/844; 514/919; 514/937; 514/938; 516/21; 516/53

(58) Field of Search .................. 424/59, 400, 401, 424/405, DIG. 10; 514/844, 919, 937, 938; 516/21, 53

(56) References Cited

U.S. PATENT DOCUMENTS 6,391,290 B1 * 5/2002 Fowler .................. 424/59

* cited by examiner

*Primary Examiner*—Shelley A. Dodson
(74) *Attorney, Agent, or Firm*—Robert J. Lipka

(57) ABSTRACT

Disclosed are skin care compositions that are emulsion formulations comprising an aqueous phase, an oil phase, at least one emulsifier, and an epichlorohydrin cross-linked glyceryl starch.

8 Claims, 2 Drawing Sheets

Malvern Instruments

| Upper | in | Lower | Under | Upper | in | Lower | Under | Upper | in | Lower | Under | Span | |
|---|---|---|---|---|---|---|---|---|---|---|---|---|---|
| | | | | | | | | | | | | 2.24 | |
| | | | | 36.3 | 0.0 | 31.4 | 100 | 6.18 | 6.9 | 5.33 | 66.7 | | |
| | | | | 31.4 | 0.0 | 27.1 | 100 | 5.33 | 7.7 | 4.60 | 59.0 | D[4,3] | |
| | | | | 27.1 | 0.0 | 23.3 | 100 | 4.60 | 8.0 | 3.97 | 50.9 | 4.95μm | |
| | | | | 23.3 | 0.1 | 20.2 | 99.8 | 3.97 | 8.0 | 3.42 | 42.9 | | |
| 118 | 0.0 | 102 | 100 | 20.2 | 0.6 | 17.3 | 99.2 | 3.42 | 7.9 | 2.95 | 35.0 | D[3,2] | |
| 102 | 0.0 | 88.2 | 100 | 17.3 | 1.3 | 15.0 | 97.9 | 2.95 | 7.4 | 2.55 | 27.6 | 2.67μm | |
| 88.2 | 0.0 | 76.0 | 100 | 15.0 | 2.4 | 12.9 | 95.5 | 2.55 | 6.9 | 2.19 | 20.7 | | |
| 76.0 | 0.0 | 65.6 | 100 | 12.9 | 3.4 | 11.1 | 92.1 | 2.19 | 5.3 | 1.90 | 15.4 | D[v,0.9] | |
| 65.6 | 0.0 | 56.6 | 100 | 11.1 | 3.8 | 9.63 | 88.3 | 1.90 | 3.9 | 1.64 | 11.5 | 10.26μm | |
| 56.6 | 0.0 | 48.8 | 100 | 9.63 | 4.2 | 8.31 | 84.1 | 1.64 | 2.5 | 1.41 | 8.9 | | |
| 48.8 | 0.0 | 42.1 | 100 | 8.31 | 4.8 | 7.16 | 79.2 | 1.41 | 1.5 | 1.22 | 7.4 | D[v,0.1] | |
| 42.1 | 0.0 | 36.3 | 100 | 7.16 | 5.7 | 6.18 | 73.5 | 1.22 | 7.4 | 0.32 | 0.0 | 1.51μm | |
| Source = | | :Sample | | Beam length = | | 2.2 mm | | Model indp | | | | D[v,0.5] | |
| | | | | Log. Diff. = | | 2.465 | | | | | | 3.90μm | |
| Focal length = | | 63 mm | | Obscuration = | | 0.2822 | | Volume Conc. = 0.0134% | | | | | |
| Presentation = pil | | | | Volume distribution | | | | Sp.S.A 2.2461 m²/cc. | | | | Shape OFF | |

Malvern Instruments

SKIN CARE COMPOSITIONS

This appcation is a continuation of U.S. patent application Ser. No. 09/813,614, filed on Mar. 21, 2001 and now U.S. Pat. No. 6,391,290, from which benefit of priority is hereby formally claimed.

BACKGROUND OF THE INVENTION

A wide variety of compositions are known in the art for providing cosmetic and/or pharmacologic benefits to human skin. Benefits sought include, for example, prevention, treatment or amelioration of environmental or age-related damage or deterioration of the skin, improved appearance by modifying surface characteristics, improved feel by moisturizing, and prevention or treatment of specific skin disorders. Many conventional cosmetic cream and lotion compositions are described, for example, in Sagarin, Cosmetics Science and Technology, 2nd Edition, Volume 1, Wiley lnterscience (1972), and Encyclopedia of Chemical Technology, Third Edition, Volume 7.

Starch derived from various plant sources has been commonly known in the art to provide a desirable skin feel in emulsions intended for topical use. While providing the desirable skin feel, the efficiency and performance of unmodified starch can be erratic. This had led to the development of various types of cross-linked and surface modified starches. One of these in wide use is modified with aluminum octenylsuccinate; an example brand of this is trademarked Dri-Flo by National Starch Inc. Although an improvement over unmodified starch, the material can cause excessive thickening of product when heated and the stability of some cold process emulsions (Pemulen systems) is compromised with use of this material.

Accordingly, there is a need for a topical formulation containing a modified starch that will impart desirable skin feel upon application to the skin, yet will also withstand the elevated temperatures during formulation and not cause excessive thickening of the resulting formulation.

In addition to the need for such a topical formulation, it would be advantageous to use these formulations as vehicles for both sunscreen and after sun formulations.

It is now generally recognized that exposure to solar radiation can have adverse health consequences, sometimes not appearing until several years following the exposure. Of course, the immediately appearing "sunburn" from an overexposure can itself be a serious acute health problem.

Many products are available to reduce the amount of solar ultraviolet radiation received by the skin during exposure to the sun's rays. Typical product formulations are lotions, creams, ointments or gels containing chemical and/or physical barriers to ultraviolet transmission. These vary considerably in their abilities to protect the skin against the physical and biochemical effects of ultraviolet radiation.

Earlier sunscreening formulations were designed to protect against sunburn from a limited solar exposure period, while transmitting sufficient radiation to permit skin tanning. However, the current focus is on eliminating as much ultraviolet exposure as possible, it being recognized that skin tanning, while esthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

The SPF (Sun Protection Factor) rating system has been developed to provide consumer guidance in selecting suitable sunscreens for any given outdoor activity. In general, the SPF number approximately corresponds to the multiple of time during which the properly applied sunscreen will prevent obvious reddening of the skin, over the exposure time that causes unprotected skin to exhibit reddening. Thus, a person should be able to remain in the sun without visible effects for eight times the usual unprotected duration, if an SPF 8 sunscreen formulation has been properly applied. Of course, the duration of unprotected exposure which produces a visible effect on the skin varies from one individual to another, due to differences in their skin cells. Currently popular are high-SPF "sunblocker" products, having SPF values of at least 30.

One particular disadvantage of sunscreen products is developing a formulation containing sunscreen active agents that does not impart an oily feel when applied to the user's skin. Accordingly, it would be advantageous to have a formulation containing sunscreen active agents that imparts an elegant feel upon application to the user's skin. Similarly, non sunscreen emulsions can also have the disadvantage of an oily skin feel. Accordingly, it would also be advantageous to have a non sunscreen formulation that imparts an elegant feel upon application to the users skin, such as after sun and insect repellant formulations, either alone or in combination with a sunscreen active agent.

SUMMARY OF THE INVENTION

Accordingly the present invention provides an emulsion formulation for topical application to the skin comprising an aqueous phase, an oil phase, at least one emulsifier, and an epichlorohydrin cross-linked glyceryl starch.

The invention further provides an oil-in-water emulsion formulation for topical application to the skin comprising an aqueous phase, an oil phase, at least one emulsifier, and an epichlorohydrin cross-linked glyceryl starch.

The invention further provides a water-in-oil emulsion formulation for topical application to the skin comprising an aqueous phase, an oil phase, at least one emulsifier, and an epichlorohydrin cross-linked glyceryl starch.

The invention further provides an emulsion formulation for topical application to the skin comprising an aqueous phase, an oil phase, at least one emulsifier, an epichlorohydrin cross-linked glyceryl starch and at least one sunscreen active agent.

The invention further provides an oil-in-water emulsion formulation for topical application to the skin comprising an aqueous phase, an oil phase, at least one emulsifier, an epichlorohydrin cross-linked glyceryl starch and at least one sunscreen active agent.

The invention also provides an oil-in-water formulation for topical application to the skin comprising an aqueous phase, an oil phase, at least one emulsifier, an epichlorohydrin cross-linked glyceryl starch, and an insect repellant.

Finally, the invention further provides an oil-in-water formulation for topical application to the skin comprising an aqueous phase, an oil phase, at least one emulsifier, an epichlorohydrin cross-linked glyceryl starch, at least one sunscreen sunscreen active agent, and an insect repellant.

DETAILED DESCRIPTION OF THE INVENTION

Figure 1:
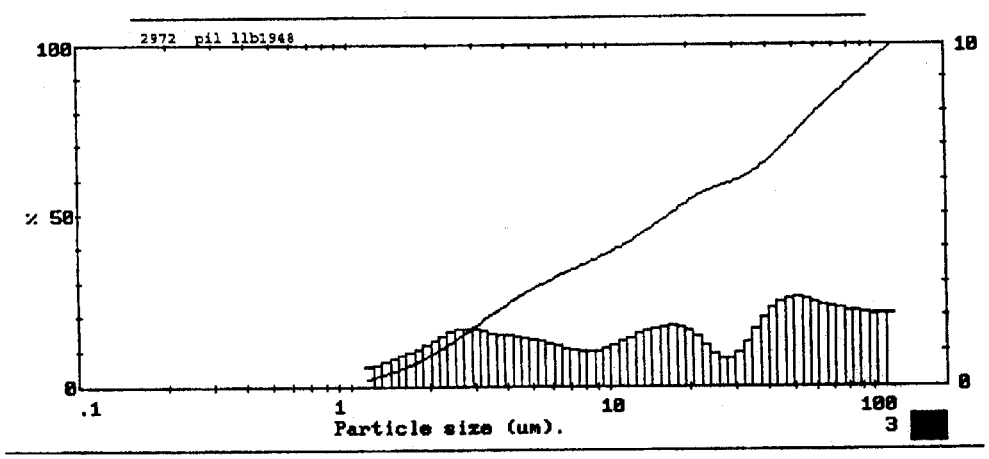
FIG. 1 is an analysis performed by Malvern Instruments concerning the particle size distribution of the emulsion droplets contained in a formulation that contains Dri-Flo starch.

Names given to chemical substances herein generally are either accepted chemical names, or are trade organization or regulatory agency approved names such as CTFA Adopted Names as listed in J. A. Wenninger et al., Eds., CTFA International Cosmetic Ingredient Dictionary, Eighth Ed., The Cosmetic, Toiletry and Fragrance Association, Washington, D.C., 2000.

The term "percent by weight" as used herein means the percent by weight of the ingredient per weight of the overall formulation.

The term epichlorohydrin cross-linked starch refers to glyceryl starch that has been chemically cross-linked by epichlorohydrin to produce a starch that has excellent tolerance to processing variables such as heat and shear. The starch has a desirable smooth texture and feel, and possesses improved stability relative to other starches commonly known in the art. The formulation maintains a viscosity profile that is less variable than that of other starches that are commonly known in the art throughout formulation and shelf-life. The preferred epichlorohydrin cross-linked glyceryl starch is sold under the trade name Vulca 90 or PC 99-1054, available from National Starch & Chemical Corp., and under the trade name Stabilex-M, available from INA Concepts, Charlotte, N.C. The epichlorohydrin cross-linked glyceryl starch may be present in an amount of about 0.1 percent to about 50 percent by weight, preferably about 2 percent to about 5 percent by weight, most preferably about 3 or 4 percent by weight.

The epichlorohydrin cross-linked starch may be prepared according to the examples of U.S. Pat. No. 4,237,271, issued in the name of Rayford, et al., which is hereby incorporated by reference in its entirety, and which discloses methods of manufacturing cross-linked starch halohydrins and their nitrogen containing substitution products.

The epichlorohydrin cross-linked glyceryl starch is a modified corn starch that is a fine whitish powder. Additionally, the starch can have about 13% maximum of water content, and a neutral pH in a 10% slurry. The starch can have a 0.5% maximum ash content. Moreover, it is advantageous that the starch have low amounts of residue propylene chlorohydrins, in the magnitude of about 0.20 to about 30 ppm propylene chlorohydrins in the final product of the starch. As is known to one of skill in the art, these amounts are subject to some variation. For personal care applications, the starch may be irradiated prior to formulation to reduce the microbial load, as is well known in the art.

The term "emulsion" shall be used herein to identify oil-in-water (o/w) or water-in-oil (w/o) type dispersion formulations intended for application to the skin, particularly lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, sunless tanning agents and the like, depending on the intended uses for the formulations.

Techniques for forming o/w and w/o emulsions are very well known in the art. The present invention is not dependent upon any particular formulation technique, it being recognized that the choice of specific formulation components may well make necessary some specific formulation procedure.

Suitable emulsifiers for one aspect of the invention are those known in the art for producing oil-in-water and/or water-in-oil type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase, and assists with both the formation and the maintenance, or stability, of the emulsion. Suitable emulsifiers for another aspect of the invention are those known in the art for producing water-in-oil type emulsions. The typical water-in-oil emulsifier has a HLB value of about 4 to about 6, as is well known in the art; however, this "rule" is also known to have numerous exceptions. Selection of suitable water-in-oil emulsifiers is well known in the formulation art.

Most of the widely used emulsifier systems for sunscreen formulations can be used in the invention. Particularly preferred emulsifiers are PEG-8 Distearate available under the trade name of Emerest 2712 from Henkel, PEG-5 Glyceryl Stearate available under the trade name POEM-S-105 from Riken Vitamin Oil, PEG-6 Hydrogenated Castor Oil, available under the trade name Sabowax ELH6 from Sabo, PEG-6 Oleate, available under the trade name STEPAN PEG-300 MO from Stepan, Sorbitan Sesquioleate, available under the trade name Arlacel 83 and Arlacel C from ICI Surfactants, TEA-Stearate, available under the trade name of Cetasal from Gaftefosse S.A. Another preferred emulsifier is neutralized cetyl phosphate, available under the trade name Amphisol A from LaRoche. Most preferred is an Acrylate/$C_{10}$–$C_{30}$ alkyl acrylate cross polymer of $C_{10-30}$ alkyl acrylates and one or more monomers of acrylic acid, methacrylic acid or one of their simple esters crosslinked within allyl ether of sucrose or an allyl ether of pentaerythritol, available under the trade names of Pemulen TR from B.F. Goodrich. The amount of emulsifier used in the present invention is present in an amount of about 0.1 to about 10% by weight, preferably about 0.5 percent to about 5 percent by weight, most preferably about 2 percent to about 4 percent by weight. The choice of an emulsifier is well within ordinary skill in the art and is not a critical aspect of the invention. Additional preferred emulsifiers that may be employed include Sorbitan Triisostearate available under the trade name Crill 6 from Croda Oleochemicals, and Polyglyceryl-3 Distearate available under the trade name Cremophor GS 32 from BASF.

Notwithstanding the Examples as set forth below, compositions of the present invention containing the epichlorohydrin cross-linked starch may be formulated by dispersing the epichlorohydrin cross-linked starch into the oil phase of the formulation when manufacturing the compositions of the present invention, and then combining this phase with the water phase in forming an oil-in-water emulsion within the scope of the present invention. Many variations of formulating the compositions of the present invention exist, and all are considered within the scope of the present invention.

As is known in the art, it is preferred that the individual emulsion droplets have a small and uniform size because these properties result in a more stable emulsion. Conversely, a broad particle size distribution indicates that the interfacial tension between the droplets has not been substantially reduced, and thus the droplets tend to coalesce and form agglomerations that result in an unstable emulsion.

Figure 2:
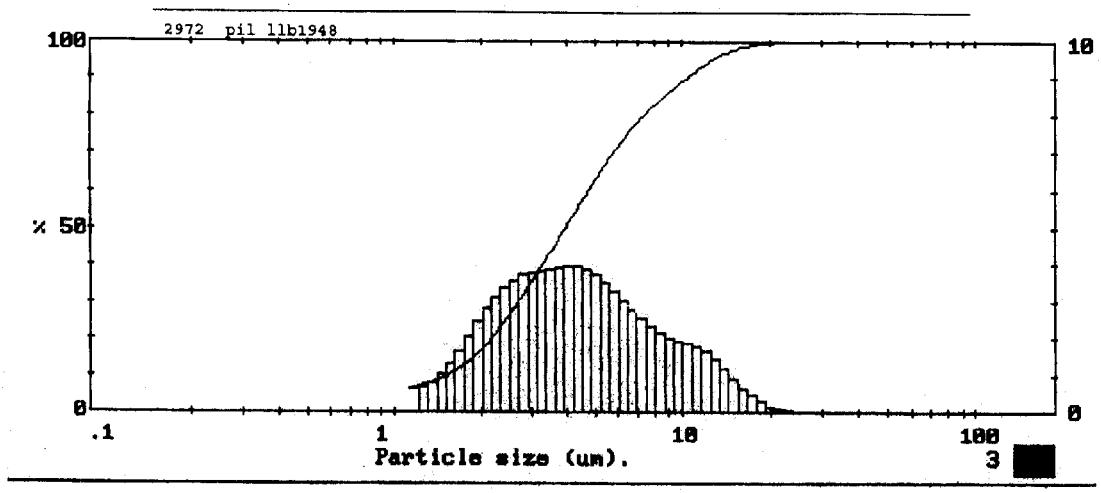
FIG. 2 is an analysis performed by Malvern Instruments concerning the particle size distribution of the emulsion droplets contained in a formulation that contains the epichlorohydrin cross-linked glyceryl starch.

An analysis performed by Malvern Instruments comparing Dri-Flo starch to the epihlorohydin cross-linked glyceryl starch of the present invention is shown in FIGS. 1 and 2. In FIG. 1, the formulation containing the Dri-Flo starch has an emulsion droplet diameter varying over a wide particle size range of from about 1 micron to about 100 microns. There is a 90% distribution of particle size below about 83 microns as indicated in FIG. 1 and the accompanying analysis below.

As indicated in FIG. 2, however, there is a much narrower distribution of particle size with 90% of the emulsion droplets having a particle size of less than about 10 microns in a formulation containing the epichlorohydrin cross-linked glyceryl starch of the present invention.

Thus, while not intending to be bound by any theory of operability, it is believed that these characteristics provide the desired enhanced skin feel and improved processability and stability of formulations containing the epichlorohydrin cross-linked glyceryl starches of the present invention.

An analysis was performed on the two formulations using a shaker. The formulations were pre-heated at 40° C. for two hours and then shaken at 180 rpm at 40° C. Qualitative assessment was made at 2 hour intervals for a period of up to 8 hours. The data is presented below in Table 1. The lack of the presence of oil (N/O) is indicative of improved stability of the formulation over time.

TABLE 1

| Description | First Oil Seen | Oil in Tube | Oil Squeezed Up |
| --- | --- | --- | --- |
| Hours at 180 rpm @ 40 C. (2.0 hr preheat then shake, Read every 2 hours up to 8 hours | | | |
| CT oil free Faces Lotion SPF30 containing Dri-Flo | 8 | 8 | 8 |
| CT oil free Faces Lotion SPF30 containing Vulca 90 | N/O | N/O | N/O |

As is evident, the formulation containing the epichlorohydrin cross-linked glyceryl starch of the present invention had no oil at the end of testing, while the formulation containing the Dri-Flo evidenced phase separation at 8 hours.

A second test was performed and the results are presented below in Table 2.

TABLE 2

| Description | First Oil | Oil in Tube | Oil Squeezed Up |
| --- | --- | --- | --- |
| Hours at 180 rpm @ 40 C. (2.0 hr preheat then shake, Read every 2 hours up to 8 hours | | | |
| CT oil free Faces Lotion SPF30 containing Dri-Flo | 2 | 2 | 2 |
| CT oil free Faces Lotion SPF30 containing Vulca 90 | N/O | 8 | N/O |

Again, the formulation containing the epichlorohydrin cross-linked glyceryl starch of the present invention displayed markedly improved results relative to the formulation containing the Dri-Flo.

The formulations of the present invention provide an elegant feel upon application to the skin, while also possessing an improved ability to withstand high temperature and shear during formulation, as well as, improved stability over time relative to other skin care products currently manufactured.

The emulsions of the present invention have many advantages over prior art formulations. The emulsions of the present invention have improved stability characteristics because of the smaller, more uniform emulsion droplet size. There is a decrease in any large change in viscosity that frequently occurs with other types of starches. Moreover, the use of the epichlorohydrin cross-linked glyceryl starch provides a formulation having decreased viscosity fluctuation in the formulation and is more inert as compared to other starches known in the art.

For purposes of the present invention, a "sunscreen active agent" shall include all of those materials, singly or in combination, that are regarded as acceptable for use as active sunscreening ingredients. Approval by a regulatory agency is generally required for inclusion of active agents in formulations intended for human contact, and those active agents which have been or are currently approved for sunscreen use in the United States include, without limitation, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum.

Particularly preferred sunscreen active agents include homomenthyl salicylate available under the trade name Uniderm Homsal from Universal Preserv-A-Chem, Benzophenone-3, available under the trade name Escalol 567 from ISP VanDyk, Uvinul MS-40 from BASF and Uvasorb MET/C from 3V Inc., Octyl Salicylate available under the trade name Neo Heliopan OS from Haarmann & Reimer, Octocrylene available under the trade name Uvinul N-539-SG from BASF and the trade name Neo Heliopan 303 from Haarmann & Reimer, and Octyl methoxcinnamate, available under the trade name Parsol MCX from Givaudon Roure and LaRoche, or mixtures thereof.

It is typical to use combinations of two or more sunscreen ingredients in a formulation, to achieve higher levels of ultraviolet absorption or to provide useful absorption over a wider range of ultraviolet wavelengths than can be the case with a single active component. Several other sunscreen active ingredients are accepted for use in other countries and are also considered to be within the scope of the present invention.

Insect repelling components are desirable in sunscreening emulsions, since the emulsions are normally used primarily by persons engaged in outdoor activities. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

As used herein, an after sun emulsion formulation is defined as a formulation that can be administered after a user has been in the sun for any amount of time that provides a soothing or healing effect that is pleasant to the user. Such a formulation can contain, for instance, aloe vera, vitamins A and E, etc.

The compositions of the present invention may contain a wide range of additional, optional components. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, waterproofing agents, and viscosity increasing agents (aqueous and nonaqueous).

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 percent to 95 weight percent, preferably from about 45 to 75 percent, most preferably from about 60 percent to about 75 percent.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$–$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight.

A dry-feel modifier is an agent which when added to an emulsion, imparts a "dry feel" to the skin when the emulsion dries. Dry feel modifiers can be used in addition to the epichlorohydrin cross-linked glyceryl starch used in the formulation of the present invention. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A.

It may be advantageous to incorporate additional thickening agents, such as, for instance, Carbopol Ultrez, or alternatively, Carbopol ETD 2001, available from the B.F. Goodrich Co. The selection of additional thickening agents is well within the skill of one in the art.

A waterproofing or water resistance agent is a hydrophobic material that imparts film forming and waterproofing characteristics to an emulsion. A suitable waterproofing agent is a copolymer of vinyl pyrollidone and eicosene and dodecane monomers such as Ganex V 220 and Ganex V 216 Polymers, respectively, trade names of ISP Inc. of Wayne, N.J. U.S.A. Still other suitable waterproofing agents include polyurethane polymer, such as Performa V 825 available from New Phase Technologies and polyanhydride resin No. 18 available under the trade name PA-18 from Chevron. The waterproofing agent is used in amounts effective to allow the sunscreen to remain effective on the skin after exposure to circulating water for at least 40 minutes for water resistance and at least 80 minutes for waterproofing using the procedures described by the U.S. Food and Drug Administration in "Sunscreen Drug Products for OTC Human Use," Federal Register, Vol. 43, Aug. 25, 1978, Part 2, pp. 38206–38269.

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Typical preservatives include the lower alkyl esters of para-hydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton. One or more antimicrobial preservatives can optionally be included in an amount ranging from about 0.001 to about 10 weight percent, preferably about 0.05 to about 1 percent.

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, Vitamin E and Vitamin C. One or more antioxidants can optionally be included in the sunscreen composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.2 weight percent preferably about 0.01% weight percent.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. The preferred fragrances for use in the present invention are Fragrance SZ-2108 and Fragrance SZ-1405 available from Sozio, Inc.. One or more fragrances can optionally be included in the sunscreen composition in an amount ranging from about 0.001 to about 5 weight percent, preferably about 0.01 to about 0.5 percent by weight.

A pH modifier is a compound that will adjust the pH of a formulation to a lower, e.g., more acidic pH value, or to a higher, e.g., more basic pH value. The selection of a suitable pH modifier is well within the ordinary skill of one in the art.

The invention will be further described by means of the following examples, which are not intended to limit the invention, as defined by the appended claims, in any manner.

In each of the foregoing examples, the dispersator is of the open shear blade type, for instance, a Premier Model 50 dispersator.

EXAMPLE 1

| Percent W/W | Ingredient Description |
|---|---|
| | Part A |
| 56.86 | USP Purified Water |
| 0.12 | Carbopol Ultrez 10 |
| | Part B |
| 5.00 | Sorbitol Solution, 70% USP |
| 0.01 | Disodium EDTA |
| 1.11 | Triethanolamine, 99% NF |
| | Part C |
| 0.05 | Vitamin E, DL Alpha Tocopherol |
| 0.80 | Polyanhydride Resin PA-18 |
| 0.80 | Stearic Acid, NF Trip Pressed |
| 0.60 | Cremophor GS-32 |
| 1.50 | Crill 6 |
| 12.00 | Homomenthyl Salicylate; Homosal |
| 5.50 | UVASORB; UVINUL M40; Escalol 567 |
| 5.00 | Neo Heliopan OS |
| 0.40 | D.C. 200 Fluid 350 CS |
| 0.70 | Ganex V220 Polymer |
| 5.00 | Octocrylene |
| | Part D |
| 0.05 | Fragrance SZ-2108 |
| 1.00 | Germaben II |
| | Part E |
| 3.00 | Vulca PC99-1054 |

The formulation is manufactured by adding the carbopol to the water of Part A while stirring and mixing until the mixture is clear and lump-free. Next, the ingredients of Part B are added to Part A and the resulting mixture is heated to 170–180° F. The temperature of the mixture is maintained. Next, the ingredients of Part C are mixed together, with the exception of the PA-18 and D.C. 200 Fluid, and heated to 180–185° F. The PA-18 is sprinkled into Part C and mixed until the PA-18 is dissolved. Finally, the D.C. 200 fluid is added to the mixture of Part D. Next, the hot oil phase of Step 3 is added to the hot water phase of Step 2. When the batch cools to less than 122° F., part D is added to the mixture and mixing is continued until the batch reaches room temperature. Next part E is slowly sprinkled into the emulsion. QS batch and mix well.

EXAMPLE 2

| Percent W/W | Ingredient Description |
|---|---|
| | Part A |
| 58.36 | USP Purified Water |
| 0.12 | Carbopol Ultrez 10 |
| | Part B |
| 5.00 | Sorbitol Solution, 70% USP |
| 0.01 | Disodium EDTA |
| 1.11 | Triethanolamine, 99% NF |
| | Part C |
| 0.05 | Vitamin E, DL Alpha Tocopherol |
| 0.80 | Polyanhydride Resin PA-18 |
| 0.80 | Stearic Acid, NF Trip Pressed |
| 0.60 | Cremophor GS-32 |
| 1.50 | Crill 6 |
| 12.00 | Homomenthyl Salicylate; Homosal |
| 5.50 | UVASORB; UVINUL M40; Escalol |

| Percent W/W | Ingredient Description |
| --- | --- |
| | 567 |
| 5.00 | Neo Heliopan OS |
| 0.40 | D.C. 200 Fluid 350 CS |
| 0.70 | Ganex V220 Polymer |
| 5.50 | Octocrylene |
| | Part D |
| 0.05 | Fragrance SZ-2108 |
| 1.00 | Germaben II |
| | Part E |
| 3.00 | Vulca PC99-1054 |

The formulation is manufactured by adding the carbopol to the water of Part A while stirring and mixing until the mixture is clear and lump-free. Next, the ingredients of Part B are added to Part A and the resulting mixture is heated to 170–180° F. The temperature of the mixture is maintained. Next, the ingredients of Part C are mixed together, with the exception of the PA-18 and D.C. 200 Fluid, and heated to 180–185° F. The PA-18 is sprinkled into Part C and mixed until the PA-18 is dissolved. Finally, the D.C. 200 fluid is added to the mixture of Part D. Next, the hot oil phase of Step 3 is added to the hot water phase of Step 2. When the batch cools to less 122° F., part D is added to the mixture and mixing is continued until the batch reaches room temperature. Next part E is slowly sprinkled into the emulsion. QS batch and mix well.

EXAMPLE 3

| Percent W/W | Ingredient Description |
| --- | --- |
| | Part A |
| 55.66 | USP Purified Water |
| 3.00 | Glycerin, USP, 99% |
| | Part B |
| 5.00 | Neo Heliopan OS |
| 5.00 | Myritol 331 |
| 6.00 | UVASORB; UVINUL M40; Escalol 567 |
| 12.00 | Homomenthyl Salicylate; Homosal |
| 7.50 | Parsol MCX or Neoheliopan AV |
| 1.00 | Emulgade PL 68/50 |
| | Part C |
| 0.10 | Pemulen TR-2 |
| | Part D |
| 0.75 | 10% Sodium Hydroxide |
| | Part E |
| 0.05 | Fragrance SZ-2108 |
| 1.00 | Germaben II |
| | Part F |
| 3.00 | Vulca PC99-1054 |

In a container large enough to hold the entire batch, add the ingredients of Part A. Mix completely and heat to 175° F. In a separate container, add the ingredients of Part B and heat to 180° F. Sprinkle in Part C into the container containing Part B. Add the mixture of Parts B and C into Part A and thoroughly mix. Add Part D to the resulting mixture. Allow the mixture to cool to 122° F., and then add Part E. Mix thoroughly and allow the mixture to cool to room temperature. Upon cooling to room temperature, slowly sprinkle in Part F and mix well. QS the batch with water and mix thoroughly.

EXAMPLE 4

| Percent W/W | Ingredient Description |
| --- | --- |
| | Part A |
| 55.85 | USP Purified Water |
| 3.00 | Glycerin, USP, 99% |
| | Part B |
| 5.00 | Neo Heliopan OS |
| 5.00 | Myritol 331 |
| 6.00 | Uvasorb; Uvinul M40; Escalol 567 |
| 12.00 | Homomenthyl Salicylate; Homosal |
| 7.50 | Parsol MCX or Neo Heliopan AV |
| 1.00 | Emulgade PL 68/50 |
| | Part C |
| 0.10 | Pemulen TR-2 |
| | Part D |
| 0.50 | 10% Sodium Hydroxide |
| | Part E |
| 1.00 | Germaben II |
| 0.05 | Fragrance SZ-2108 |
| | Part F |
| 3.00 | Vulca PC99-1054 |

In a container large enough to hold the entire batch, add ingredients of Part A. Mix completely and heat to 175° F. In a separate container, add the ingredients of Part B and heat to 180° F. Sprinkle in Pemulen TR 2 of Part C into Part B. Add Part B/Part C mixture to Part A with thorough mixing. Add 10% NaOH of Part D. When cooled to 122° F., add Part E. Mix thoroughly and slowly sprinkle in Part F while mixing. When cooled to room temperature, QS the batch with water and homogenize for 5 minutes.

EXAMPLE 5

| Percent W/W | Ingredient Description |
| --- | --- |
| | Part A |
| 56.00 | USP Purified Water |
| 3.00 | Glycerin, USP, 99% |
| | Part B |
| 5.00 | Neo Heliopan OS |
| 5.00 | Myritol 331 |
| 6.00 | Uvasorb; Uvinul M40; Escalol 567 |
| 12.00 | Homomenthyl Salicylate; Homosal |
| 7.50 | Parsol MCX or Neo Heliopan AV |
| 1.00 | Emulgade PL 68/50 |
| | Part C |
| 0.10 | Pemulen TR-2 |
| | Part D |
| 0.35 | 10% Sodium Hydroxide |
| | Part E |
| 1.00 | Germaben II |

-continued

| Percent W/W | Ingredient Description |
|---|---|
| 0.05 | Fragrance SZ-2108 |
| | Part F |
| 3.00 | Vulca PC99-1054 |

In a container large enough to hold the entire batch, add ingredients of Part A. Mix completely and heat to 175° F. In a separate container, add the ingredients of Part B and heat to 180° F. Sprinkle in Pemulen TR 2 of Part C into Part B. Add Part B/Part C mixture to Part A with thorough mixing. Add 10% NaOH of Part D. When cooled to 122° F., add Part E. Mix thoroughly and slowly sprinkle in Part F while mixing. When cooled to room temperature, QS the batch with water and homogenize for 5 minutes.

EXAMPLE 6

| Percent W/W | Ingredient Description |
|---|---|
| | Part A |
| 56.89 | USP Purified Water |
| 0.09 | Carbopol Ultrez 10 |
| | Part B |
| 5.00 | Sorbitol Solution, 70% USP |
| 0.01 | Disodium EDTA |
| 1.11 | Triethanolamine, 99% NF |
| | Part C |
| 0.05 | Vitamin E, DL Alpha Tocopherol |
| 0.80 | Polyanhydride Resin PA-18 |
| 0.80 | Stearic Acid, NF Trip Pressed |
| 0.60 | Cremophor GS-32 |
| 1.50 | Crill 6 |
| 12.00 | Homomenthyl Salicylate; Homosal |
| 5.50 | UVASORB; UVINUL M40; Escalol 567 |
| 5.00 | Neo Heliopan OS |
| 0.40 | D.C. 200 Fluid 350 CS |
| 0.70 | Ganex V220 Polymer |
| 5.50 | Octocrylene |
| | Part D |
| 0.05 | Fragrance SZ-2108 |
| 1.00 | Germaben II |
| | Part E |
| 3.00 | Vulca PC99-1054 |

The formulation is manufactured by adding the carbopol to water of Part A while stirring and mixing until the mixture is clear and lump-free. Next, the ingredients of Part B are added to Part A and the resulting mixture is heated to 170–180° F. The temperature of the mixture is maintained. Next, the ingredients of Part C are mixed together, with the exception of the PA-18 and D.C. 200 Fluid, and heated to 180–185° F. The PA-18 is sprinkled into Part C and mixed until the PA-18 is dissolved. Finally, the D.C. 200 fluid is added to the mixture of Part D. Next, the hot oil phase of Step 3 is added to the hot water phase of Step 2. When the batch cools to less than 122° F., Part D is added to the mixture and mixing is continued until batch reaches room temperature. Next Part E is slowly sprinkled into the emulsion. QS the batch and mix well.

EXAMPLE 7

| Percent W/W | Ingredient Description |
|---|---|
| | Part A |
| 56.88 | USP Purified Water |
| 0.10 | Carbopol Ultrez 10 |
| | Part B |
| 5.00 | Sorbitol Solution, 70% USP |
| 0.01 | Disodium EDTA |
| 1.11 | Triethanolamine, 99% NF |
| | Part C |
| 0.05 | Vitamin E, DL Alpha Tocopherol |
| 0.80 | Polyanhydride Resin PA-18 |
| 0.80 | Stearic Acid, NF Trip Pressed |
| 0.60 | Cremophor GS-32 |
| 1.50 | Crill 6 |
| 12.00 | Homomenthyl Salicylate; Homosal |
| 5.50 | UVASORB; UVINUL M40; Escalol 567 |
| 5.00 | Neo Heliopan OS |
| 0.40 | D.C. 200 Fluid 350 CS |
| 0.70 | Ganex V220 Polymer |
| 5.50 | Octocrylene |
| | Part D |
| 0.05 | Fragrance SZ-2108 |
| 1.00 | Germaben II |
| | Part E |
| 3.00 | Vulca PC99-1054 |

Add Carbopol to water of Part A while stirring and mix until the mixture is clear and lump-free. Add the ingredients of Part B to Part A and heat to 170–180° F. Maintain the temperature of the mixture. Mix the ingredients of Part C together except for PA-18 and D.C. 200 fluid, and heat to 180–185° F. Sprinkle in the PA-18 and mix until the PA-18 is dissolved, and then add the D.C. 200 fluid. Add the hot oil phase of Step 3 to the hot water phase of Step 2. When the batch cools to less than 122° F., add Part D and continue mixing until the batch reaches room temperature. Slowly sprinkle Part E into the emulsion. QS the batch and mix well.

EXAMPLE 8

| Percent W/W | Ingredient Description |
|---|---|
| | Part A |
| 46.81 | USP Purified Water |
| 0.30 | Pemulen TR-2 |
| 0.01 | Disodium EDTA |
| 0.10 | Tween 20 |
| 1.50 | Germazide MPB |
| | Part B |
| 2.00 | Parsol 1789 |
| 5.00 | Octocrylene |
| 4.00 | Uvasorb; Uvinul M40; Escalol 567 |
| 5.00 | Neo Heliopan OS |
| 8.00 | Homomenthyl Salicylate; Homosal |
| 6.00 | Cetiol OE |
| 2.00 | D.C. 200 Fluid 350 CS |
| 2.00 | Ganex v216 |
| 0.01 | Aloe Vera Lip-/Aloe Oil Extr. |
| 0.01 | Vitamin E, DL Alpha Tocopherol |
| | Part C |

-continued

| Percent W/W | Ingredient Description |
|---|---|
| 10.00 | USP Purified Water |
| 0.25 | Triethanolamine, 99% NF |
| | Part D |
| 4.00 | Vulca PC99-1054 |
| | Part E |
| QS | USP Purified Water |

Add the ingredients of Part A except for the Pemulen to a beaker and mix. Slowly sprinkle in the Pemulen and mix until it is completely dispersed. Add the ingredients of Part B to a second beaker and heat with mixing to 135–145° F. until all of the Oxybenzone has dissolved. Add the oil phase to the water phase and mix with a high speed disperser for a minimum of 15 minutes at 2700 rpms. Combine the water and TEA of Part of C and mix until all of the TEA has dissolved. The resulting solution should be clear. Change to a 3 blade prop and continue mixing the primary emulsion of step 4. Add the TEA solution of Step 5 to the primary emulsion and mix vigorously for 3 minutes. Slowly sprinkle in the Vulca PC99-1054 of Part D and stir vigorously for at least 15 minutes. QS the batch to weight with the water of Part E and mix for 1 minute.

EXAMPLE 9

| Percent W/W | Ingredient Description |
|---|---|
| | Part A |
| 48.54 | USP Purified Water |
| 0.30 | Pemulen TR-2 |
| 3.00 | Polyethylene Glycol 400, NF |
| 0.20 | Methylparaben, NF |
| 0.01 | Disodium EDTA |
| 0.10 | Tween 20 |
| 0.50 | Benzyl Alcohol, NF |
| | Part B |
| 2.00 | Parsol 1789 |
| 5.00 | Octocrylene |
| 4.00 | Uvasorb; Uvinul M40; Escalol 567 |
| 5.00 | Neo Heliopan OS |
| 8.00 | Homomenthyl Salicylate; Homosal |
| 6.00 | Cetiol OE |
| 2.00 | D.C. 200 Fluid 350 CS |
| 2.00 | Ganex V-216 |
| 0.10 | Propylparaben, NF |
| | Part C |
| 10.00 | USP Purified Water |
| 0.25 | Triethanolamine, 99% NF |
| | Part D |
| 3.00 | Vulca PC99-1054 |
| | Part E |
| QS | USP Purified Water |

Add the ingredients of Part A except the Pemulen to a beaker and mix. Slowly sprinkle in the Pemulen and mix until it is completely dispersed. Add the ingredients of Part B to a second beaker and heat with mixing to 135–145° F. until all of the Oxybenzone has dissolved. Add the oil phase to the water phase and mix with a high speed disperser for a minimum of 15 minutes at 2700 rpms. Combine the water and TEA of Part of C and mix until all has dissolved. The resulting solution should be clear. Change to a 3 blade prop and continue mixing the primary emulsion of Step 4. Add the TEA solution of Step 5 to the primary emulsion and mix vigorously for 3 minutes. Slowly sprinkle in the Vulca PC99-1054 of Part D and stir vigorously for at least 15 minutes. QS the batch to weight with the water of Part E and mix for 1 minute.

EXAMPLE 10

| Percent W/W | Ingredient Description |
|---|---|
| | Part A |
| 47.54 | USP Purified Water |
| 0.30 | Pemulen TR-2 |
| 3.00 | Polyethylene Glycol 400, NF |
| 0.20 | Methylparaben, NF |
| 0.01 | Disodium EDTA |
| 0.10 | Tween 20 |
| 0.50 | Benzyl Alcohol, NF |
| | Part B |
| 2.00 | Parsol 1789 |
| 5.00 | Octocrylene |
| 4.00 | Uvasorb; Uvinul M40; Escalol 567 |
| 5.00 | Neo Heliopan OS |
| 8.00 | Homomenthyl Salicylate; Homosal |
| 6.00 | Cetiol OE |
| 2.00 | D.C.200 Fluid 350 CS |
| 2.00 | Ganex V-216 |
| 0.10 | Propylparaben, NF |
| | Part C |
| 10.00 | USP Purified Water |
| 0.25 | Triethanolamine, 99% NF |
| | Part D |
| 4.00 | Vulca PC99-1054 |
| | Part E |
| QS | USP Purified Water |

Add the ingredients of Part A except the Pemulen to a beaker and mix. Slowly sprinkle in the Pemulen and mix until it is completely dispersed. Add the ingredients of Part B to a second beaker and heat with mixing to 135–145° F. until all of the Oxybenzone has dissolved. Add the oil phase to the water phase and mix with a high speed disperser for a minimum of 15 minutes at 2700 rpms. Combine the water and TEA of Part C and mix until all has dissolved. The resulting solution should be clear. Change to a 3 blade prop and continue mixing the primary emulsion of Step 4. Add the TEA solution of Step 5 to the primary emulsion and mix vigorously for 3 minutes. Slowly sprinkle in the Vulca PC99-1054 of Part D and stir vigorously for at least 15 minutes. QS the batch to weight with the water of Part E and mix for 1 minute.

EXAMPLE 11

| Percent W/W | Ingredient Description |
|---|---|
| | Part A |

-continued

| Percent W/W | Ingredient Description |
|---|---|
| 49.54 | USP Purified Water |
| 0.30 | Pemulen TR-2 |
| 3.00 | Polyethylene Glycol 400, NF |
| 0.20 | Methylparaben, NF |
| 0.01 | Disodium EDTA |
| 0.10 | Tween 20 |
| 0.50 | Benzyl Alcohol, NF |
| | Part B |
| 2.00 | Parsol 1789 |
| 5.00 | Octocrylene |
| 4.00 | Uvasorb; Uvinul M40; Escalol 567 |
| 5.00 | Neo Heliopan OS |
| 4.00 | Acetylated Lanolin Alcohol |
| 2.00 | Glucam P-20 Distearate |
| 7.00 | Finsolv TN |
| 2.00 | D.C.200 Fluid 350 CS |
| 2.00 | Ganex V-216 |
| 0.10 | Propylparaben, NF |
| | Part C |
| 10.00 | USP Purified Water |
| 0.25 | Triethanolamine, 99% NF |
| | Part D |
| 3.00 | Vulca PC99-1054 |
| | Part E |
| QS | USP Purified Water |

Add the ingredients of Part A except the Pemulen to a beaker and mix. Slowly sprinkle in the Pemulen and mix until it is completely dispersed. Add the ingredients of Part B to a second beaker and heat with mixing to 135–145° F. until all of the Oxybenzone has dissolved. Add the oil phase to the water phase and mix with a high speed disperser for a minimum of 15 minutes at 2700 rpms. Combine the water and TEA of Part C and mix until all has dissolved. The resulting solution should be clear. Change to a 3 blade prop and continue mixing the primary emulsion of Step 4. Add the TEA solution of Step 5 to the primary emulsion and mix vigorously for 3 minutes. Add the Vulca PC99-1054 of Part D with vigorously agitation. Mix vigorously for at least 15 minutes. QS the batch to weight with the water of Part E and mix for 1 minute. Hand-mill the entire batch.

EXAMPLE 12

| Percent W/W | Ingredient Description |
|---|---|
| | Part A |
| 64.20 | USP Purified Water |
| 0.40 | Pemulen TR-1 |
| 0.15 | Carbopol ETD 2001 |
| 0.20 | Methylparaben, NF |
| | Part B |
| 0.01 | Disodium EDTA |
| | Part C |
| 3.00 | Octocrylene |
| 2.00 | Parsol 1789 |
| 5.00 | Neo Heliopan OS |
| 10.00 | Homomenthyl Salicylate; Homosal |

-continued

| Percent W/W | Ingredient Description |
|---|---|
| 0.05 | Vitamin E, DL Alpha Tocopherol |
| 0.05 | Aloe Vera Lipo-/Aloe Oil Extr. |
| 0.10 | Propylparaben, NF |
| 4.00 | UVASORB; UVINUL M40; Escalol 567 |
| 2.00 | Lexorez 200 |
| | Part D |
| 1.00 | Benzyl Alcohol, NF |
| | Part E |
| 0.34 | Triethanolamine, 99% NF |
| | Part F |
| 2.00 | Vulca PC99-1054 |
| 5.00 | Polyethylene Glycol 400, NF |
| | Part G |
| 0.50 | Fragrance SZ 1405 |

Using a prop mixer equipped with a small tooth blade, disperse the Pemulen and Carbolpol ETD 2001 into the water of Part A using rapid mixing for five minutes, and then change to a 3 prong prop and mix until the mixture is free from lumps. Next, add the Methylparaben and mix well. Add the Disodium EDTA of Part B to the Pemulen/Carbopol ETD 2001 solution of Step 1 and mix well. In a beaker equipped with a prop mixer, combine the ingredients of Part C and heat to 120° F. with mixing until the Spectrasorb UV-9 is dissolved. Add the oil phase of Step 3 to the aqueous phase of Step 2 and mix well. Add the Benzyl alcohol of Part D to the batch of Step 4 and mix well. Add the TEA of Part E and mix vigorously until an emulsion is formed. In a suitable sized beaker, add the PEG 400 of Part F and begin mixing on a mechanical stirrer. Slowly sprinkle in the Vulca PC99-1054 and mix vigorously until it is well dispersed. Add the suspension of Step 7 to the batch of Step 6 with vigorous agitation for at least 15 minutes. Add the fragrance of Part G and mix well.

EXAMPLE 13

| Percent W/W | Ingredient Description |
|---|---|
| | Part A |
| 67.20 | USP Purified Water |
| 0.40 | Pemulen TR-1 |
| 0.15 | Carbopol ETD 2001 |
| 0.20 | Methylparaben, NF |
| | Part B |
| 0.01 | Disodium EDTA |
| | Part C |
| 3.00 | Octocrylene |
| 5.00 | Neo Heliopan OS |
| 2.00 | Parsol 1789 |
| 2.00 | UVASORB; UVINUL M40; Escalol 567 |
| 10.00 | Homomenthyl Salicylate; Homosal |
| 0.05 | Vitamin E, DL Alpha Tocopherol |
| 0.05 | Aloe Vera Lipo-/Aloe Oil Extr. |
| 0.10 | Propylparaben, NF |
| 2.00 | Lexorez 200 |

-continued

| Percent W/W | Ingredient Description |
|---|---|
| | Part D |
| 0.34 | Triethanolamine, 99% NF |
| | Part F |
| 2.00 | Vulca PC99-1054 |
| 5.00 | Polyethylene Glycol 400, NF |
| | Part G |
| 0.50 | Fragrance SZ 1405 |

Using a prop mixer equipped with a small tooth blade, disperse the Pemulen and Carbolpol ETD 2001 into the water of Part A using rapid mixing for five minutes, and then change to a 3 prong prop and mix until free from lumps. Next, add the Methylparaben and mix well. Add the Disodium EDTA of Part B to the Pemulen/Carbopol ETD 2001 solution of Step 1 and mix well. In a beaker equipped with a prop mixer, combine the ingredients of Part C and heat to 120° F. with mixing until all of the ingredients have dissolved. Add the oil phase of Step 3 to the aqueous phase of Step 2 and mix well. Add the TEA of Part D and mix vigorously until an emulsion is obtained. In a suitable sized beaker, add the PEG 400 of Part F and begin mixing on a mechanical stirrer. Slowly sprinkle in the Vulca PC99-1054 and mix until uniform. Add the suspension of Step 6 to the batch of Step 5 with vigorous agitation for at least 15 minutes. Add the fragrance of Part G and mix well.

What is claimed is:

1. An emulsion formulation for topical application to the skin comprising: an aqueous phase, an oil phase, at least one emulsifier, and an epichlorohydrin cross-linked glyceryl starch.

2. The formulation of claim 1, wherein the formulation is an oil-in water emulsion.

3. The formulation of claim 2, wherein the at least one emulsifier is present in an amount of about 1 to about 10 percent by weight.

4. The formulation of claim 1, wherein the formulation is a water-in-oil emulsion.

5. The formulation of claim 4, wherein the at least one emulsifier is present in an amount of about 1 to about 10 percent by weight.

6. The formulation of claim 1, wherein the epichlorohydrin cross-linked glyceryl starch is present in an amount of about 0.1 to about 50 percent by weight.

7. The formulation of claim 6, wherein the epichlorohydrin cross-linked glyceryl starch is present in an amount of about 2 to about 4 percent by weight.

8. The formulation of claim 1, further comprising at least one sunscreen active agent.

* * * * *